United States Patent [19]
Smith et al.

[11] Patent Number: 5,217,595
[45] Date of Patent: Jun. 8, 1993

[54] ELECTROCHEMICAL GAS SENSOR

[75] Inventors: Matthew L. Smith, Kettering; Steven J. Fondriest, Beavercreek, both of Ohio

[73] Assignee: The Yellow Springs Instrument Company, Inc., Yellow Springs, Ohio

[21] Appl. No.: 782,597

[22] Filed: Oct. 25, 1991

[51] Int. Cl.⁵ .............................. G01N 27/26
[52] U.S. Cl. ................... 204/412; 204/422; 204/406
[58] Field of Search ............ 204/412, 406, 422

[56] References Cited
U.S. PATENT DOCUMENTS

| | | | |
|---|---|---|---|
| 4,589,970 | 5/1986 | Ligtenberg | 204/412 |
| 5,000,180 | 3/1991 | Kuypers et al. | 204/412 |
| 5,098,547 | 3/1992 | Bryan et al. | 204/412 |
| 5,100,530 | 3/1992 | Dorr et al. | 204/412 |

Primary Examiner—John Niebling
Assistant Examiner—Bruce F. Bell
Attorney, Agent, or Firm—Biebel & French

[57] ABSTRACT

An electrochemical sensor for sensing a gas dissolved in a liquid. The sensor includes a probe having a cylindrical body and a rounded face. A working electrode, a reference electrode and an auxiliary electrode are buried in the probe body and have distal ends reaching conformingly to the face. A pulsed polarizing voltage is impressed between the auxiliary electrode and the working electrode for polarizing the probe, and a capacitor is provided for storing the charge which flows to the working electrode during periods of polarization. The concentration of the dissolved gas is determined by measuring the voltage across the capacitor.

19 Claims, 9 Drawing Sheets

ELECTROCHEMICAL GAS SENSOR

BACKGROUND OF THE INVENTION

This invention relates to improvements in electrochemical sensors of the general type disclosed in Clark, Jr. U.S. Pat. No. 2,913,386. It is useful for measuring the dissolved concentration of any of a wide range of electro-reducible or electro-oxidizable gasses in a rapid and accurate manner and finds particular utility in applications such as environmental monitoring wherein large geographical areas must be observed for identification of specific sources of pollution. For example, a sensor constructed in accordance with the present invention may generate data for a map of dissolved oxygen concentrations, while being towed around a harbor or up a moving stream.

Sensing of a dissolved gas in accordance with the teachings of Clark proceeds by positioning an anode and a cathode inside a suitable probe and placing them in contact with an electrolyte solution. The electrolyte solution is sealed against the electrodes by means of a membrane which is permeable to the gas being monitored. When the probe is immersed in a sample of the source liquid, the gas permeates the membrane and undergoes an electro-reaction at one of the electrodes while a balancing electro-reaction takes place at the other electrode. This causes an electrical current to flow from one electrode through the electrolyte and into the other electrode. Clark found that a voltage of about 0.6 volts should be maintained across the cell in order to provide the required electrode potential for measurement of oxygen.

When used in connection with the detection of oxygen, the following overall reaction takes place within Clark's cell:

$$4H^+ + O_2 + 4e^- \rightarrow 2H_2O$$

In general, the substance being measured tends to depolarize the cell. When the needed ions are available and a minimum polarizing potential is maintained across the cell, then the current flow through the electrodes is proportional to the rate at which dissolved gas is passing through the protective membrane.

Clark's teachings have provided a basis for numerous sensor probes developed over the years. Many of the developments have concentrated on improving the accuracy and the response time of the basic Clark probe and have provided a variety of techniques for measuring the current flow through the electrodes. In a paper entitled "Determination Of Oxygen Tension By Measurement Of Net Charge Transport", *IEEE Transactions On Biomedical Engineering*, November 1976, pages 472–477, Gregory L. Zick taught that the polarizing potential may be pulsed and that the current flow through the electrodes may be integrated during portions of the charging and discharging cycles to determine net charge. His circuit amplified the current flow, applied it to an A/D converter and then applied the digitized current sample to a mini-processor for waveform integration.

Zick applied the above teaching to a transcutaneous electrochemical cell which was patented under U.S. Pat. No. 4,269,684. Zick's patent discloses a computer which stores samples of the polarizing and depolarizing waveforms resulting from a polarizing pulse. The areas under the two waves are determined by digital integration, and an uncorrected value of the oxygen partial pressure is established by calculating the difference between the two waveform areas. The uncorrected partial pressure measurement is corrected for electrode drift by comparing discharge waveforms of successive pulses. FIG. 5 of the patent illustrates an analog circuit for integrating his polarizing and depolarizing waveforms.

Langdon U.S. Pat. No. 4,556,472 teaches a microcomputer system using a Clark-type sensor for sensing oxygen concentration in a pulsed fashion. Langdon also measures current flow. His system employs real time signal averaging to reduce the noise level and improve precision. He teaches the use of his device for environmental sampling and states that for oxygen, a pulse duration of from 0.5 to 3 seconds and a pulse interval of from 3 to 5 minutes or more are suitable.

Mund et al U.S. Pat. No. 4,853,091 discloses a miniaturized oxygen sensor for use with an implantable pacemaker. No diffusion membrane is employed. The disclosed device includes an arrangement of three electrodes and means for generating a pulsed polarizing voltage. One of the three electrodes functions as a reference electrode for making measurements of current flowing between the other two electrodes. The cycle time is between 0.5 and 10 seconds, and the current is integrated following a delay of 2 to 40 msec. The patent teaches that the measuring signal is not influenced by the capacitive current required for charging the double layer. A teaching of double layer physics is set out in Pons et al U.S. Pat. No. 4,783,250.

In spite of Clark's teachings and the various above-discussed extensions thereof, no fully satisfactory electrochemical sensor has been developed for long term environmental monitoring and similar applications. Currently available sensors are unable to meet harsh environmental conditions, or are deficient in speed or accuracy, or are excessively expensive. A further common problem is a high rate of gas consumption, which has necessitated either a long wait between measurements for electrode recovery or recourse to a stirring device with its attendant mechanical problems and consumption of power.

SUMMARY OF THE INVENTION

This invention provides an improved electrochemical sensor which combines a novel probe geometry with a pulse-type polarizing circuit to obtain reproducible and rapid "turn-on" and "turn-off". The electrode double layer is charged and discharged at a rate which keeps the gas diffusion wavefront within the pool of electrolyte during the time of measurement minimizing effects of convection.

During the polarization period the control circuit of this invention supplies the working electrode with a total charge comprising two distinct charge components; the first being a "polarizing" charge which induces the double layer and the second being a "Faradaic" or reaction charge which is a measure of the redox reaction. When the polarization potential is turned off, the polarization charge is recovered by the control circuit, and the apparatus of the invention proceeds to measure the net charge transfer to find the amount of reaction charge. A microprocessor multiplies the reaction charge by a constant of proportionality to determine the concentration of the gas molecules being monitored.

In order to maximize the utility of the sensor for environmental sampling the circuitry generates polarization control pulses at relatively short intervals, preferably no more than about 4 seconds apart. Furthermore in order to minimize stirring dependency the pulse width is limited to a duration which is a relatively small fraction of the pulse interval, preferably not much more than about 40 milliseconds (a fractional value of 0.01) to provide time for recovery of the electrolyte. It has also been found that reproducability of results can be obtained at such pulse widths and repetition intervals by designing the circuitry to achieve a very rapid turn-on and turn-off of the working electrode. It is believed that rapid turn-on and turn-off of the working electrode restricts the generation of hydrogen peroxide as an intermediate product during the establishment and dissipation of the double layer. Hydrogen peroxide diffuses rather quickly in the electrolyte, thereby reducing the net charge and producing an error in the measurement made by the sensor. However, whether hydrogen peroxide is or is not a principal source of measurement error, the present invention stabilizes the operation of the working electrode and improves the reproducability of measurements by providing a sensor which has three electrodes. One electrode (the cathode) serves as a working electrode, the second functions as a reference electrode, and the third (the auxiliary electrode) supplies current for balancing the current flow at the working electrode.

It is a feature of the invention that the reference electrode is shielded from the current flow between the auxiliary electrode and the cathode. This minimizes the error in double layer potential caused by the IR drop and increases the speed of double layer establishment. Consequently an extremely linear operation is achieved. The shielding also facilitates single point calibration by reducing the residual current to a very low level. As implemented in the invention the reference electrode is connected to provide a feedback signal for adjusting the polarization control voltage to compensate for the effects of current flow in the auxiliary electrode.

A preferred embodiment of the invention employs a charge retention capacitor connected for collecting a charge corresponding the net charge transferred at the working electrode. Throughout such charge collection by the capacitor the working electrode preferably is maintained at a virtual ground potential. A microprocessor controlled switching circuit applies a pulsed polarizing voltage between the auxiliary electrode and the working electrode, and this results in a flow of pulsed current to the capacitor. A second microprocessor controlled switch is provided for periodically discharging the charge retention capacitor. The voltage across the charge retention capacitor is measured by a suitable voltage sensor.

A measuring cycle commences by briefly shorting the capacitor to cause a discharge thereof. Then a polarizing potential is applied to the auxiliary electrode to cause rapid establishment of the double layer and nearly immediate commencement of a redox reaction involving the molecules of interest. The charge retention capacitor responds by collecting a first charge component equal to the polarization charge and a second charge component corresponding to the time integral of the reaction current. After the elapse of a suitably short pulse period, the auxiliary electrode is switched to a ground potential. The redox reaction then ceases, and the charge retention capacitor quickly surrenders that portion of its total charge representing the polarization charge. After this charge adjustment has been completed, the microprocessor reads the voltage across the capacitor terminals to determine the amount of the reaction charge. Thereafter, the capacitor is again discharged and a new cycle commences. A high impedance amplifier limits current flow in the reference electrode, so that the potential difference between the reference electrode and the working electrode is stabilized.

The preferred probe has a rounded face and a generally cylindrical body. A reservoir for holding a supply of electrolyte is provided by a generally circular channel in the face of the probe. A membrane is stretched across the face and is wetted across its inside surface by a thin layer of the electrolyte. This electrolyte layer is also in electrical contact with the cathode, the reference electrode and the auxiliary electrode. All three electrodes are buried in the sensor body with their distal ends reaching to, and conforming with, the curved surface of the face. The cathode is centrally positioned and is flanked on opposite sides by the other two electrodes. Thus the cathode shields the reference electrode from the auxiliary electrode. The cathode is configured to present to the electrolyte a surface area which is substantially smaller than that of the other two electrodes.

It is therefore an object of this invention to provide accurate, frequently repeated measurements of a dissolved gas concentration.

It is another object of the invention to provide an electrochemical sensor of improved geometry which has a working electrode for supplying a reaction current to a gas containing electrolyte, an auxiliary electrode for supplying an electrical current to balance the current flow at the working electrode and a reference electrode for supplying a reference potential to the working electrode.

It is another object of the invention to provide a gas sensor of the electrochemical type which stores electrical charge resulting from electrochemical reactions at a working electrode and measures the amount of a gas being consumed by the reaction by measuring the amount of stored charge.

Still another object of the invention is to provide a pulse-type oxygen sensor which has improved linearity and which requires only a single data sample for calibration.

Other objects and advantages of the invention will be apparent from the following description, the accompanying drawing and the appended claims.

DESCRIPTION OF THE PREFERRED EMBODIMENT

Figure 1:
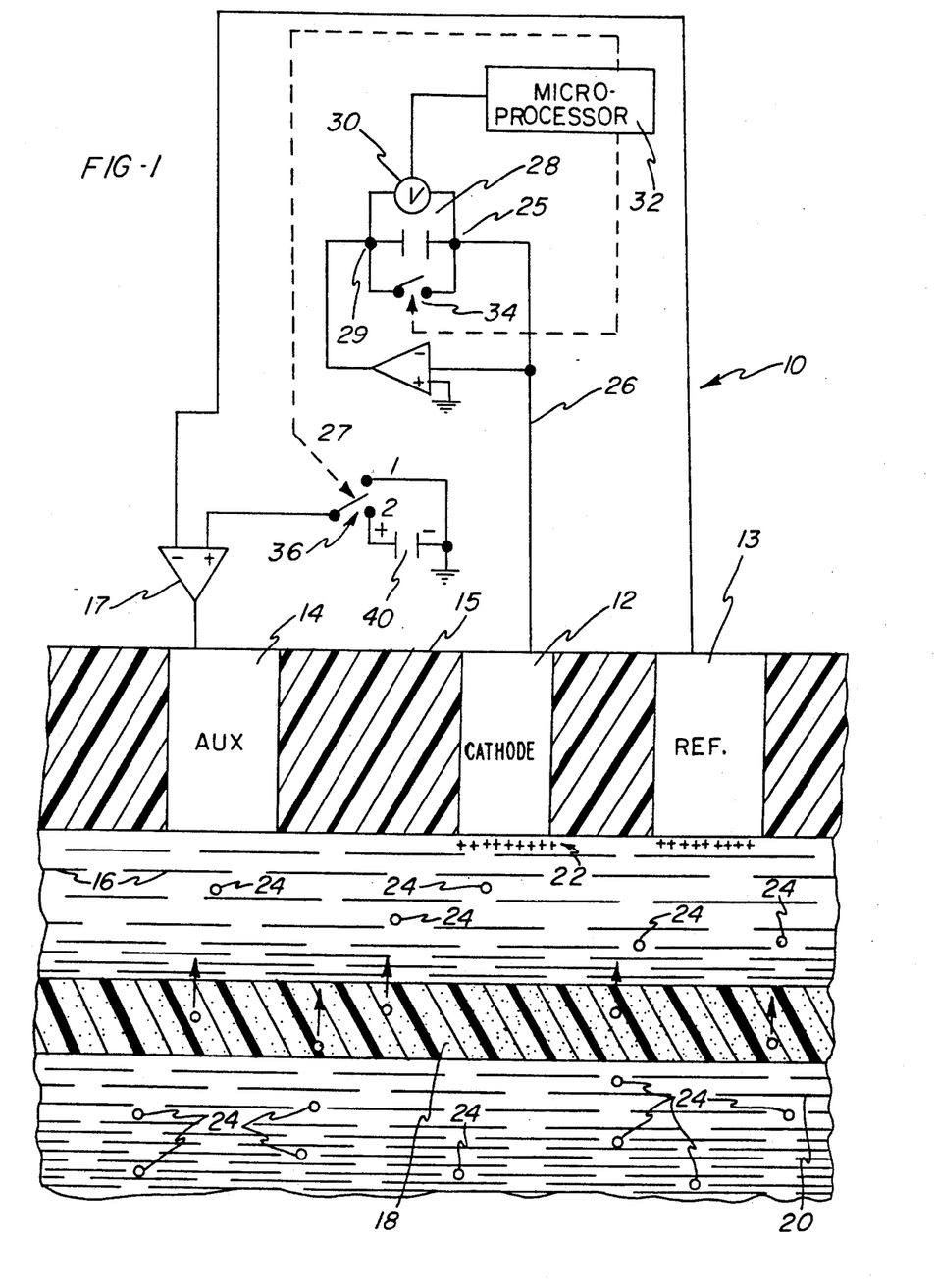
FIG. 1 is a schematic illustration of an electrochemical gas sensor in simplified form.

The operating principle of the present invention may be understood by referring to FIG. 1 which is a schematic illustration of a simplified sensor 10 comprising a cathode 12, a reference electrode 13 and an auxiliary electrode 14. Electrodes 12, 13 and 14 are embedded in a nonconductive support structure 15 and are in contact with a thin layer of an electrolyte solution 16. In the special case where the invention is used for measuring oxygen concentration, electrolyte 16 may be half saturated potassium chloride in water with a small amount of a suitable surfactant. A suitable membrane 18 confines electrolyte solution 16 within a narrow region adjacent electrodes 12, 14. A test solution 20 is placed in contact with the opposite side of membrane 18 in the manner generally taught by Clark, Jr., U.S. Pat. No. 2,913,386.

In the preferred embodiment of the invention cathode 12 is positioned so as to shield or screen reference electrode 13 from auxiliary electrode 14. This confines the electrochemical activity of the cell to the regions of the cathode and the auxiliary electrode and limits the current flow in the area of the reference electrode to a fairly low level. Consequently the cell has low IR losses, fast turnon and attendant good linearity. A sensor of this type, using pulsed polarizing circuitry as described below, can be calibrated from data at a single sample point.

Cathode 12 is constructed from a highly conductive and non-reactive material such as gold and is connected to a first terminal 25 of a charge retention capacitor 28 and to the inverting terminal of an operational amplifier 27 by a lead line 26. The non-inverting terminal of operational amplifier 27 is connected to ground and the output terminal thereof is connected to a second terminal 29 of charge retention capacitor 28. This arrangement places cathode 12 at a virtual ground potential.

Auxiliary electrode 14 is connected through differential amplifier 17 to a switch 36 which may be positioned either at ground potential or at a positive potential as determined by a potential source 40. Switch 36 operates under control of a microprocessor 32. Another switch 34 also operates under control of microprocessor 32 for selectively discharging charge retention capacitor 28. Prior to measuring the oxygen concentration, switch 34 is closed for a time sufficient to discharge capacitor 28. Then the switch is opened, and voltmeter 30 reads an initial "discharged" voltage across capacitor 28. This reading is supplied to microprocessor 32 and saved for use as hereinafter described. Reference electrode 13 is connected to a differential amplifier 17 so as to provide a negative feedback signal for auxiliary electrode 14. This adjusts the polarizing voltage of the cell to compensate for current flow effects at the auxiliary electrode.

When switch 36 is positioned for connecting auxiliary electrode 14 to potential source 40, an electrical field is established between auxiliary electrode 14 and cathode 12. This causes a flow of electrons from capacitor 28 to the surface of cathode 12. The resulting negative surface charge produces a double layer by inducing an opposing thin sheet of ions 22 in electrolyte 16. Any dissolved oxygen molecules which happen to enter the double layer are subjected to an extremely high electrical field and become reduced. The reduction process draws electrons from cathode 12, which are replaced by capacitor 28. As a consequence, capacitor acquires a charge which is the sum of two components: (1) the charge associated with establishment of the double layer (the "polarization" charge), and (2) the integrated current flow associated with the reduction of oxygen (the "reaction" charge).

It will be observed that the reaction charge is related to the concentration of oxygen in electrolyte 16 (and in test solution 20). The apparatus of FIG. 1 determines that component by terminating the redox reaction and measuring the voltage across capacitor 28, after the cell has had time to become depolarized. That involves waiting for a predetermined period of time sufficient for establishing the double layer at the cathode and getting a good redox reaction underway and then moving switch 36 to position No. 1. When this is done auxiliary electrode 14 drops to a ground potential, ion sheet 22 dissipates, the field of the double layer collapses, and the polarizing charge on the surface of cathode 12 returns to capacitor 28. This partially discharges the capacitor and leaves it with a final charge which is the above-mentioned reaction charge. Operational amplifier 27 provides an output potential sufficient to maintain that charge on the capacitor. Microprocessor 32 determines the amount of the charge by reading the output of a voltmeter 30, correcting that reading by subtracting the above-mentioned initial reading, and multiplying the corrected reading by a proportionality constant.

As oxygen molecules become reduced, thereby charging capacitor 28 the oxygen in electrolyte 16 begins to become depleted. The region of depletion begins at cathode 12 and expands progressively out into electrolyte 16. In accordance with the practice of this invention, switch 36 is operated on a cyclic basis which provides for a short period of oxygen reduction, followed by a recovery period sufficiently long to permit replenishment of the oxygen depletion region by spontaneous mass transfer processes. In the preferred embodiment as hereinafter described in detail, such measurements may be made at least every 4 seconds.

The constant of proportionality required for converting the measured voltage across capacitor 28 into an oxygen concentration measurement depends upon solution temperature, probe geometry and the timing of the switch operation. In actual operation the proportionality constant is determined by performing a calibration sequence during which sensor 10 is immersed in a solution containing a known concentration of dissolved oxygen or in water saturated air. The known concentration is fed into microprocessor 32 and stored. Then the microprocessor reads the output from voltmeter 30 and calculates the proportionality constant required for producing the known concentration from such a reading. In the preferred embodiment, as described below, a temperature sensor (not illustrated) provides frequent temperature readings, so that the microprocessor can make appropriate temperature corrections to the proportionality constant. The microprocessor also makes corrections for the solubility of oxygen through the use of algorithms well known in the art.

Figure 2:
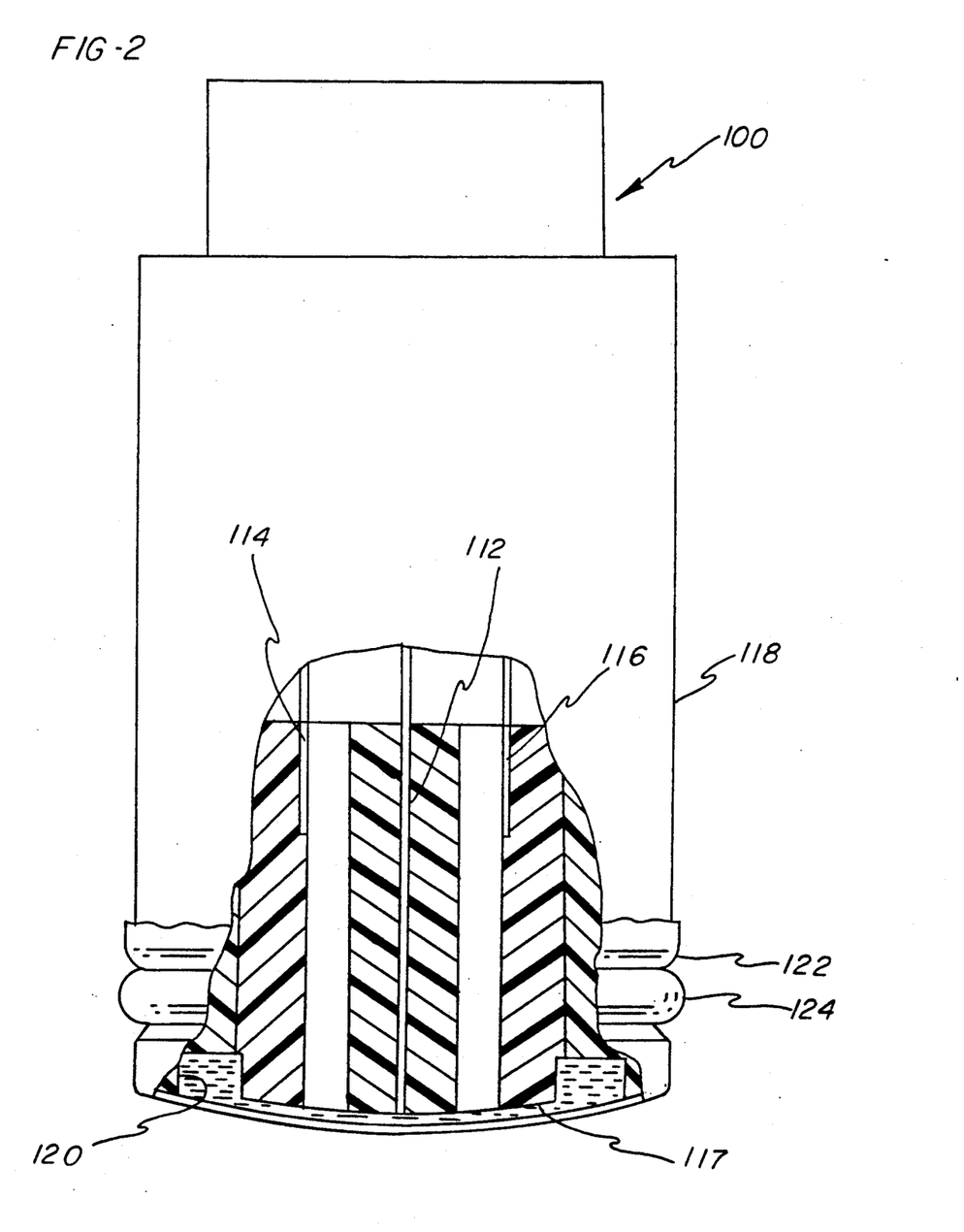
FIG. 2 is a partly cut-away side elevation view of a probe for an electrochemical gas sensor.

It will be appreciated that the arrangement of FIG. 1 is highly simplified and that the basic principles of operation incorporated therein may be applied to a wide variety of different electrode configurations and different control circuits. A preferred sensor probe 100 has an electrode arrangement as illustrated in FIG. 2 and comprises a cathode 112, a reference electrode 114 and an auxiliary electrode 116 mounted in a tubular body 118. The face 117 of body 118 has a circular channel 120 which serves as a reservoir to receive a supply of an appropriate electrolyte for the particular type of molecules being sensed. A membrane 122 is held in place around face 117 by means of an elastic band 124. Membrane 122 covers the circular channel 120 and maintains a supply electrolyte in contact with the distal ends of the three electrodes.

Figure 3A:
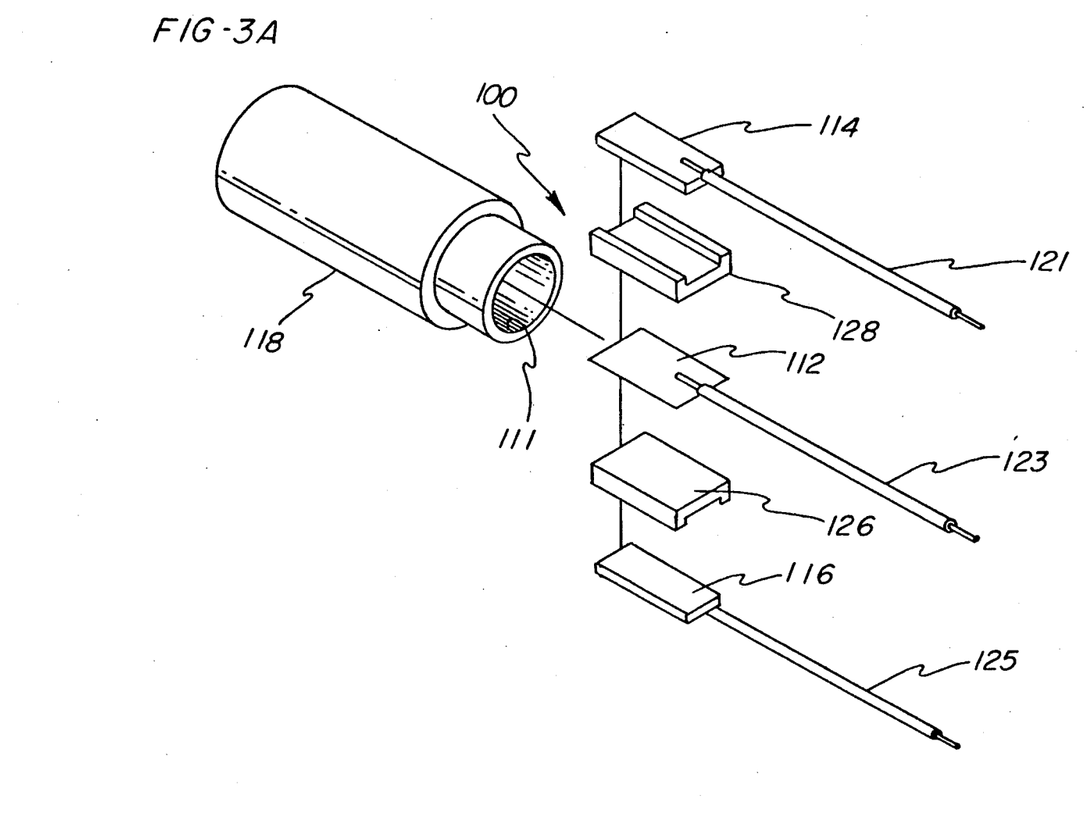
FIG. 3A is a perspective drawing of FIG. 2 showing one stage in the assembly of the sensor.

Prior to final assembly, probe body 118 appears as generally illustrated in FIG. 3A. It comprises a cast acrylic cylinder, having a reduced diameter cross-section at the rear end and a drilled axial bore 111 extending from the rear end to a point near the front of the cylinder. Cathode 112 is fabricated from gold foil having a thickness of about 0.001 in. and has a width of about 0.22 in. Reference electrode 114 and auxiliary electrode 116 are made of pure silver, and while having a somewhat narrower width than cathode 112, are considerably thicker so as to have a much greater cross-sectional area.

Figure 3B:
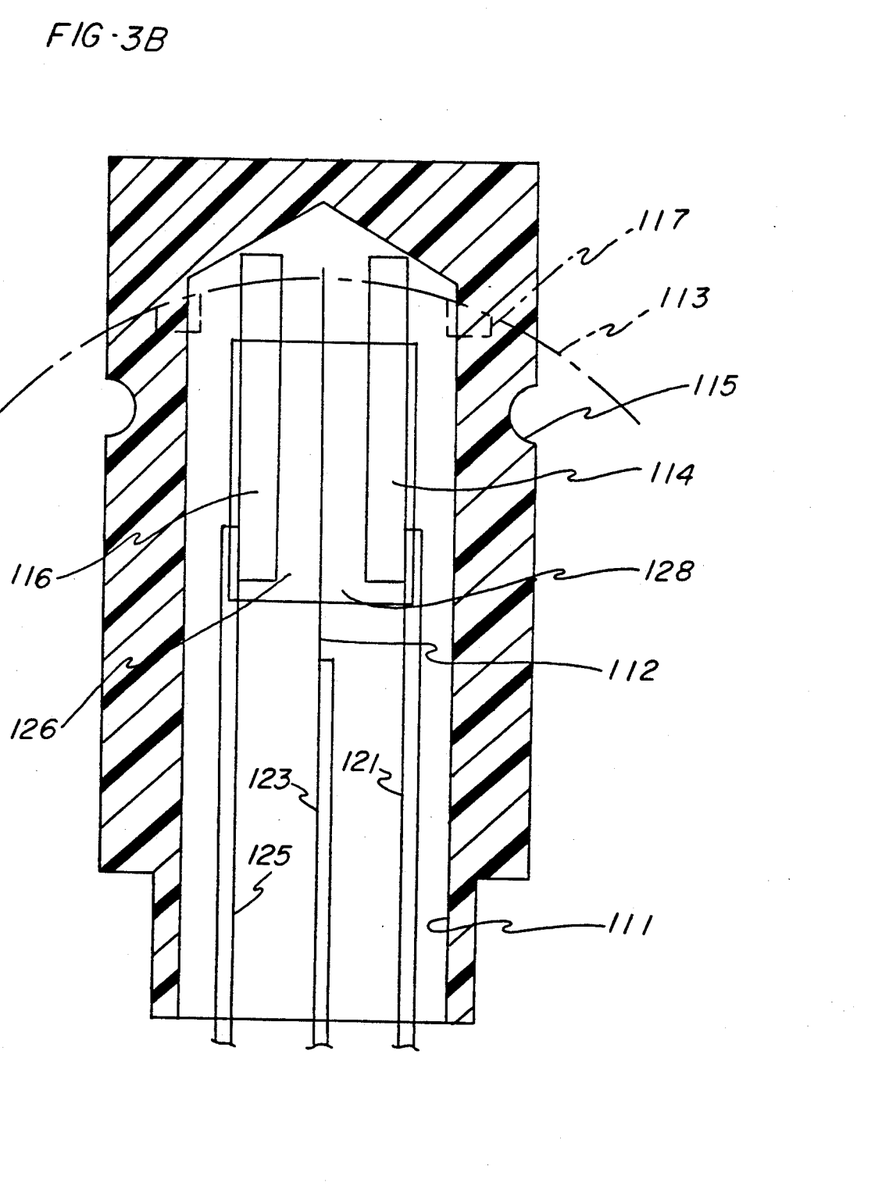
FIG. 3B is a schematic illustration of final machining operations on a sensor probe.
Figure 4:
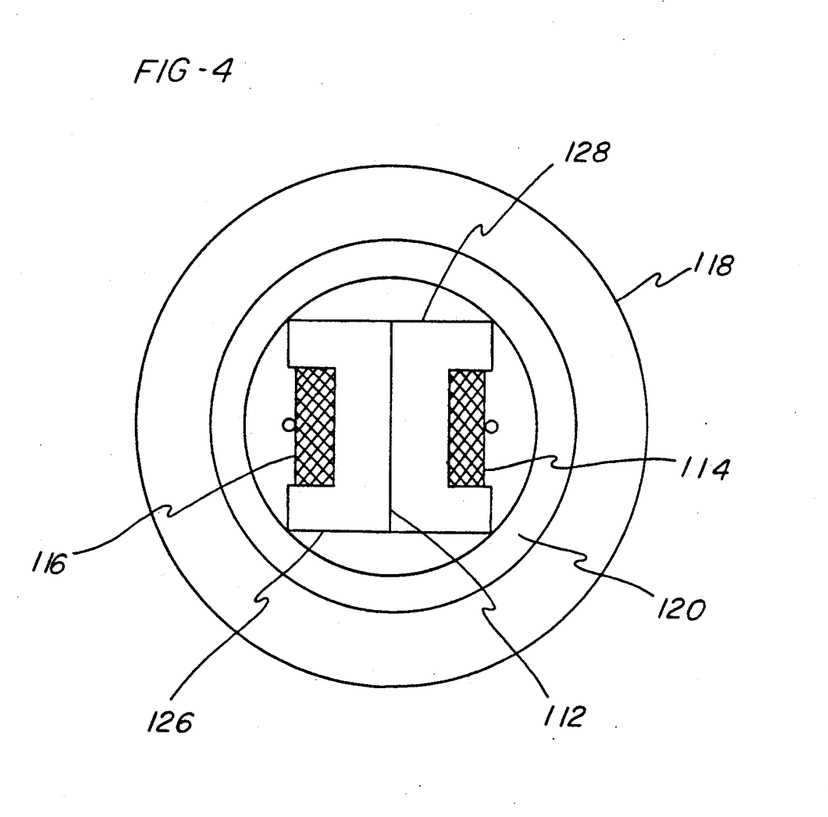
FIG. 4 is a bottom plan view of the sensor of FIG. 2 with the membrane removed.

During assembly, silver tinned wires 121,123,125 are compression welded to electrodes 114,112,116, and the electrodes are then sandwiched together between cast acrylic spacers 126,128. Then the electrode assembly is inserted into the bore 111 and cemented into place by a non-conductive epoxy. This produces an intermediate product as illustrated in FIG. 3B. The intermediate product is turned into a finished sensor probe by three machining steps. One step machines the front face 117 to define a spherical contour, as indicated by the phantom line 113. The radius of the sphere is about 1 in., while the major diameter of the probe body is about 0.5 in. This first step exposes the distal ends of the electrodes and conforms them to the spherical contour of the face. A second machining step produces the facial channel 120 by cutting along the line 117. Thirdly, a toroidal cut along the surface 115 produces a channel for gripping of membrane 122 by elastic band 124. The above-mentioned spherical radius accommodates the desired membrane tension for maintaining a film of electrolyte across the electrodes under membrane 122. A suitable membrane may be prepared from a sheet of tetrafluoroethylene about 2 mils thick.

Figure 5A:
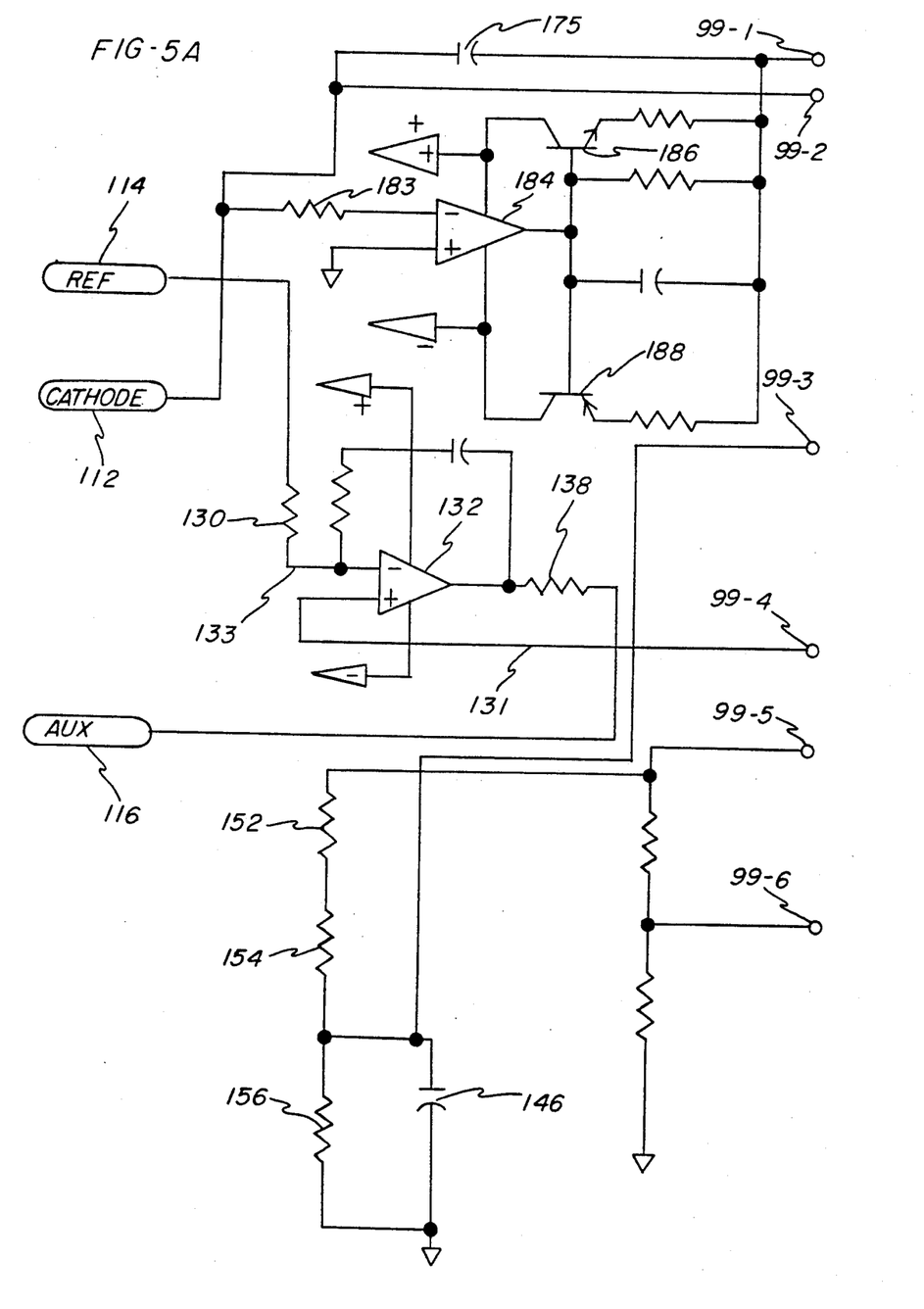
FIGS. 5A and 5B are an electrical schematic diagram of an electrochemical sensor in preferred embodiment.
Figure 5B:
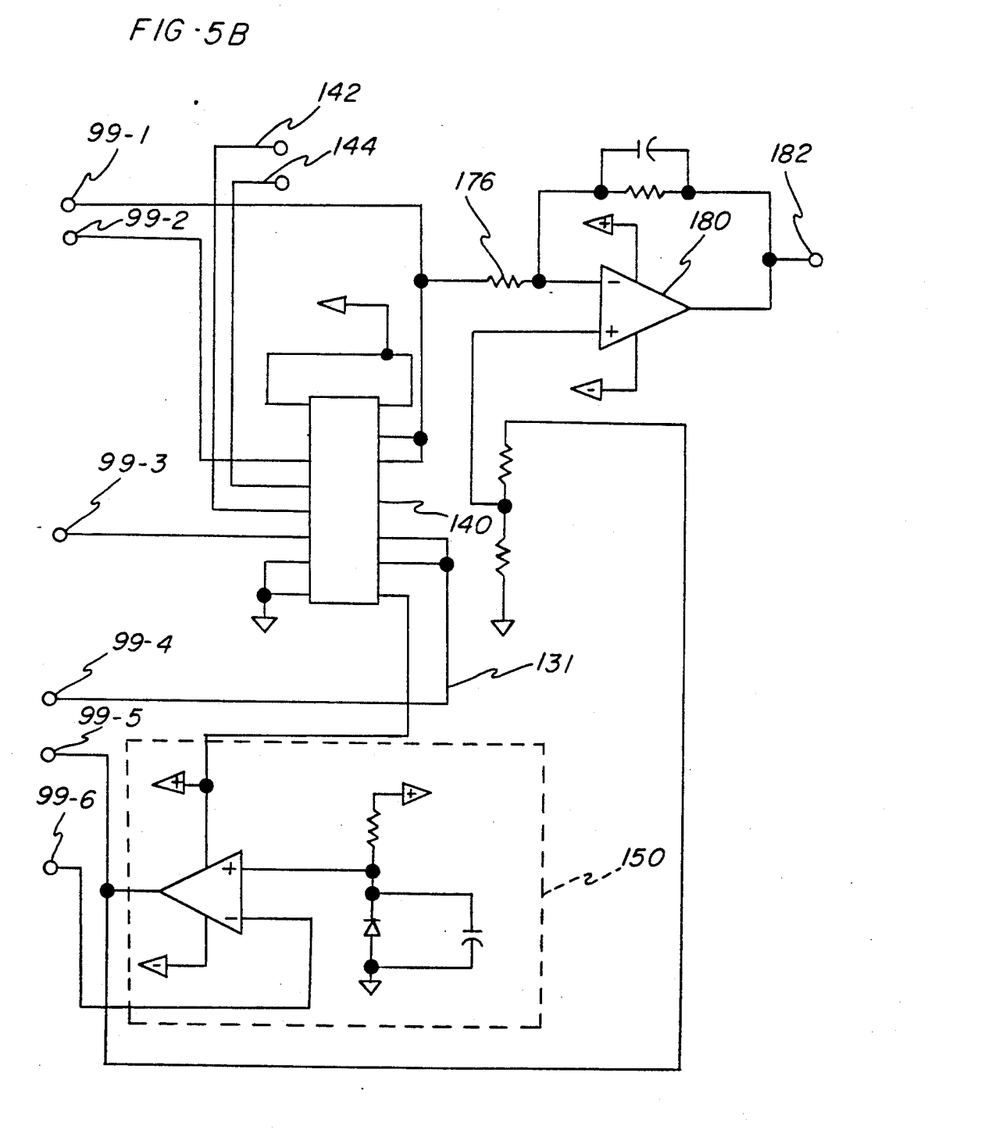

Sensing circuitry for use with probe 100 is illustrated in FIGS. 5A and 5B with connections between the two circuit portions being indicated by connection points 99-1 thru 99-6. These connection points have been added to FIGS. 5A and 5B for identification of corresponding connecting lines. No physical connector exists at the interface between the two drawing portions.

As illustrated in FIG. 5A, reference electrode 114 is connected to a high impedance operational amplifier 132. This restricts the current flow through reference electrode 114 to a very low level so as to minimize the potential drop associated with current flow between reference electrode 114 and cathode 112. Thus the potential between reference electrode 114 and cathode 112 may be controlled to a high degree of accuracy. Substantially all of the current flow required by cathode 112 flows through auxiliary electrode 116.

A resistor 130 is connected to the inverting side of operational amplifier 132 via a lead line 133. Another lead line 131 supplies the non-inverting terminal of operational amplifier 132 with a polarization control voltage from connecting point 99-4. The output side of operational amplifier 132 is connected to auxiliary electrode 116 through a resistor 138 having a resistance in the order of about 249 ohms. The circuit as illustrated sets auxiliary electrode 116 at a potential approximately equal to the potential applied to operational amplifier 132 by line 131. A small correction from reference electrode 114 is applied to the negative input terminal of operational amplifier 132.

The polarizing voltage on line 131 is controlled by an analog switch 140 which may be a type IH 5043 CMOS analog switch available commercially from Maxim Integrated Products of Sunnyvale, Calif. Switch 140 is a break-before-make device which operates under control of switching pulses received at terminals 142,144 from a microprocessor (not illustrated). A high signal on line 142 closes a switch between pins S2 and D2 of analog switch 140 thereby applying to line 131 a polarization control voltage equal to the voltage across capacitor 146. A low signal on line 142 opens the connection between pins S2 and D2 of analog switch 140 and thereafter closes a switch between pins S4 and D4 to apply a ground potential to line 131.

The voltage across capacitor 146 is supplied by a driver circuit 150 of conventional components as illustrated in FIG. 5B. The output from driver circuit 150 is preferably about 2.46 volts. This potential is dropped by current flow through resistors 152 and 154 such that the potential across capacitor 146 and its parallel resistor 156 is about 1.0 volts. Thus a high signal at line 142 produces a 1 volt potential on reference electrode 114.

A low voltage at input line 144 of analog switch 140 closes a switch between pins S3 and D3 thereby shorting out a charge retention capacitor 175. Capacitor 175 preferably has a capacitance of about 0.22 microfarad and functions in a manner similar to charge retention capacitor 28. The potential at the side of capacitor 175 remote from cathode 112 is applied to a resistor 176 connected to the inverting side of an operational amplifier 180. Operational amplifier 180 senses the voltage across capacitor 175 and supplies a corresponding output signal to an output terminal 182.

An operational amplifier 184 and a pair of transistors 186,188 perform a function similar to that described above for operational amplifier 27. Operational amplifier 184 supplies a base drive to transistor 186,188 for producing an electron flow to the remote plate of charge retention capacitor 175 which matches the flow from the capacitor to cathode 112. This creates a voltage across capacitor 175 which is proportional to the concentration of oxygen being sensed. The ground potential applied to the non-inverting terminal of operational amplifier 184 provides a virtual ground for cathode 112.

Figure 6:
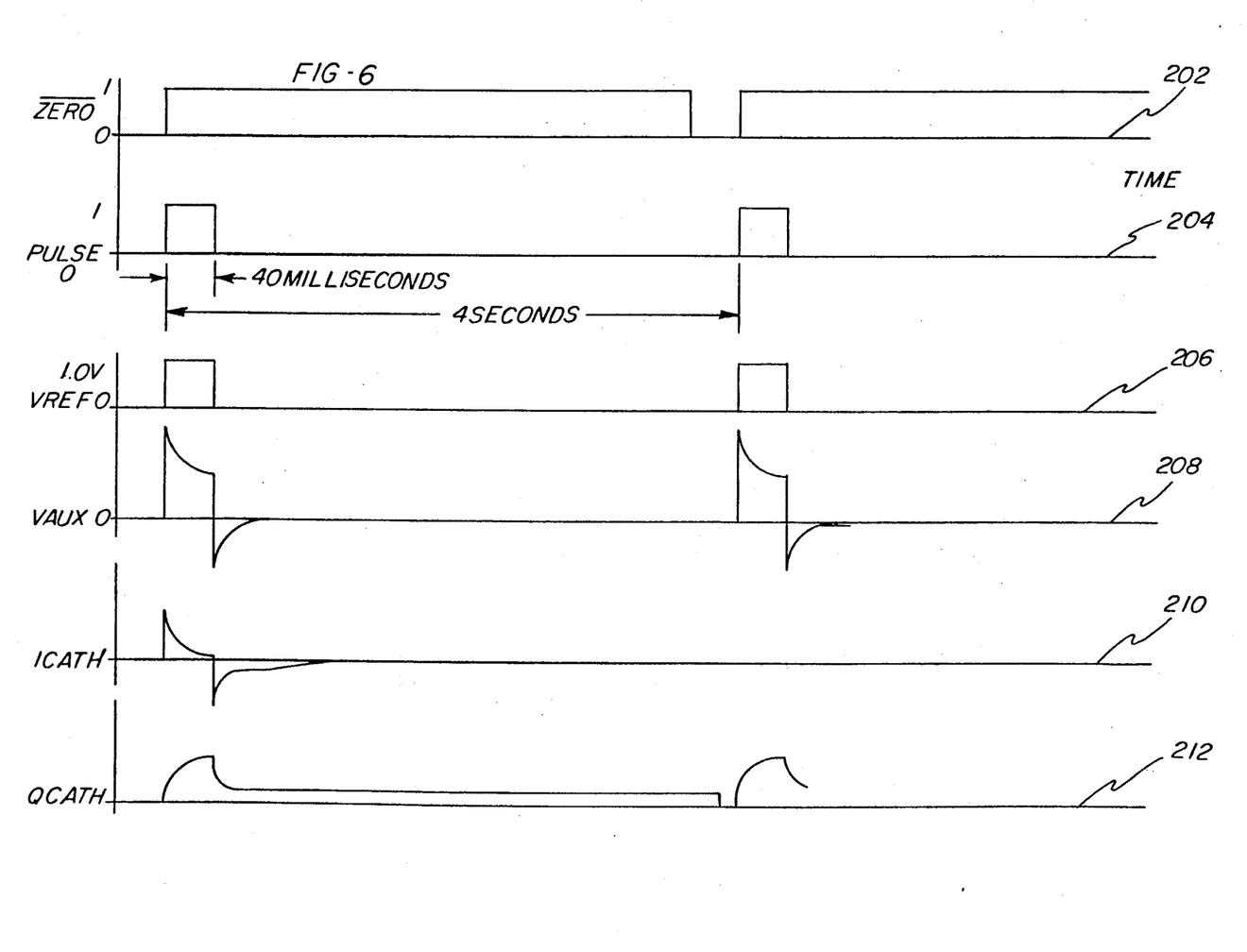
FIG. 6 is a timing diagram illustrating the operation of the circuit of FIGS. 5A and 5B.

FIG. 6 illustrates the timing sequence for the operation of the circuit of FIGS. 5A and 5B. Time line 202 illustrates the control signal applied to pin I1 of switch 140. As discussed above, this signal closes a switch which discharges charge retention capacitor 175.

Time line 204 illustrates the control signal on input pin I2 of analog switch 140. The pulses on this line preferably have a duration of about 40 milliseconds and are repeated at 4 sec. intervals. These pulses cause the application of a pulsed 1 volt potential to reference electrode 114 as illustrated by time line 206. The corresponding potential profile for auxiliary electrode 116 is illustrated by time line 208.

Time line 210 illustrates the current flow at cathode 112, and time line 212 illustrates the charge across charge retention capacitor 175. It can be seen that the charge on capacitor 175 rises rapidly in response to the application of a 1 volt potential to reference electrode 114. Then when the reference electrode is dropped to ground potential, the charge on capacitor 175 declines rapidly until it reaches a steady state value related to the concentration of oxygen molecules being sensed. This charge remains until capacitor 175 is discharged by the occurrence of another pulse on line 144.

Figure 7:
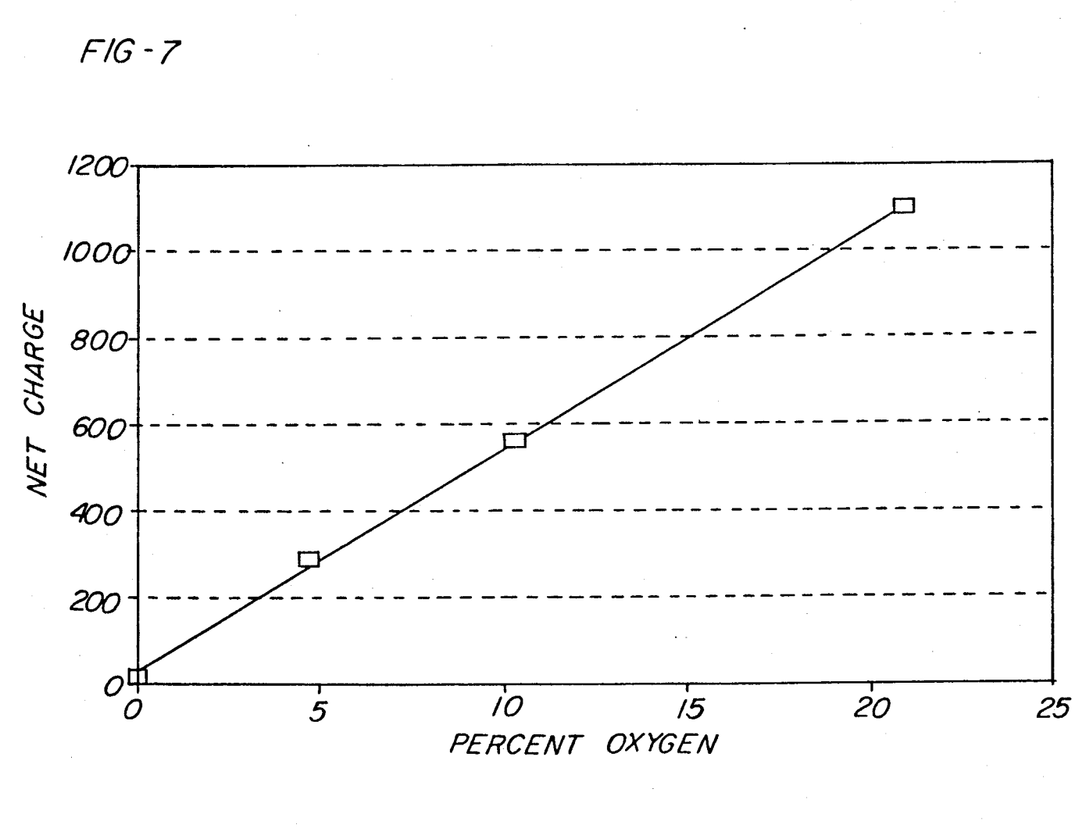
FIG. 7 is a plot net charge measurements made by a sensor of the type shown in FIGS. 2-6.

FIG. 7 illustrates test results for an oxygen sensor configured in accordance with the embodiment described above in connection with FIGS. 2 thru 6. The particular sensor used for the test employed a polarizing potential of 1.0 V which was applied to the auxiliary electrode once every 4 seconds as a pulse having a duration of 40 milliseconds. The membrane was made of tetrafluoroethylene and was 1 mil thick.

The abscissa of FIG. 7 indicates the actual oxygen content of a series of test solutions, while the ordinate indicates the net charge readings made by the microprocessor. It can be seen that the measured net charge is an extremely linear function of the oxygen content of the test solution. The particular sensing probe used for the tests of FIG. 7 gave a charge reading of 30 (residual charge) in an oxygen free environment and a reading of 1035 in a saturated air environment. Tests of other probes constructed and operated in accordance with this invention have consistently exhibited residual currents ranging between 1 and 2 percent of the saturated air reading. Thus the sensor of this invention can be calibrated using data from a single sample point.

It will be appreciated that the electrode geometry described provides simple and effective screening of the reference electrode from the auxiliary electrode. However, other arrangements could be used. For example the three electrodes could be configured as concentric cylinders and arranged with the cathode as the intermediate cylinder. Suitable screening also could be provided by a porous barrier element.

While the forms of apparatus herein described constitute a preferred embodiment of this invention, it is understood that the invention is not limited to these precise forms of apparatus, and that changes may be made therein without departing from the scope of the invention which is defined in the appended claims.

What is claimed is:

1. Apparatus for measuring the concentration of a gas dissolved in a liquid comprising:
    a probe for insertion into a sample of said liquid, said probe being provided with means for receiving a supply of an electrolyte which is a solvent for molecules of said gas and means for confining said electrolyte in contact with a membrane which is permeable by said molecules,
    a working electrode mounted within said probe for electrical contact with an electrolyte confined as aforesaid,
    an auxiliary electrode mounted within said probe for electrical contact with said electrolyte and in spaced relation with said working electrode,
    polarizing means for periodically applying between said auxiliary electrode and said working electrode, polarizing pulses of sufficient voltage for establishing an electrical field which causes molecules of said gas to undergo an electrochemical reaction and transfer an electrical charge to said working electrode,
    a reference electrode connected for supplying a reference potential to said auxiliary electrode and mounted within said probe for maintaining electrical contact with said electrolyte while being screened from said electrical field, and
    charge measuring means for measuring the net charge transferred to said working electrode during a time interval encompassing a full period of one of said pulses and the period of charging transients related thereto.

2. Apparatus for measuring the concentration of a gas dissolved in a liquid comprising:
    a probe for insertion into a sample of said liquid, said probe being provided with means defining a reservoir for receiving a supply of an electrolyte which is a solvent for molecules of said gas and means for confining said electrolyte in contact with a membrane which is permeable by said molecules,
    a working electrode mounted within said probe for electrical contact with an electrolyte confined as aforesaid,
    an auxiliary electrode mounted within said probe for electrical contact with said electrolyte and in spaced relation with said working electrode,
    polarizing means for periodically applying between said auxiliary electrode and said working electrode, polarizing pulses of sufficient voltage for establishing an electrical field which causes molecules of said gas to undergo an electrochemical reaction and transfer an electrical reaction charges to said working electrode,
    a reference electrode connected for supplying a reference potential to said auxiliary electrode and mounted within said probe for maintaining electrical contact with said electrolyte while being screened from said electrical field, and
    charge retention means connected for storing a sample of said reaction charge,
    charge measuring means for periodically measuring the charge on said charge retention means following completion of said electrochemical reaction, and
    discharge means for cyclically discharging said charge retention means following said charge measuring.

3. Apparatus according to claim 2 wherein said charge retention means comprises a capacitor.

4. Apparatus according to claim 3 and further comprising a differential amplifier having an output terminal connected to one side of said capacitor, one input terminal interconnecting a second side of said capacitor with said working electrode, and a second input terminal connected to ground, so that said operational amplifier maintains said working electrode at a virtual ground potential.

5. Apparatus according to claim 2 further comprising feedback means for applying the potential of said reference electrode as a negative feedback signal to said auxiliary electrode.

6. Apparatus for measuring the concentration of a gas dissolved in a liquid comprising:
    a probe for insertion into a sample of said liquid, said probe being provided with means defining a reservoir for receiving a supply of an electrolyte which is a solvent for molecules of said gas and means for confining said electrolyte in contact with a membrane which is permeable by said molecules, a working electrode mounted within said probe in electrical contact with said reservoir, a reference electrode mounted within said probe in electrical contact with said reservoir and in spaced relation with said working electrode, an auxiliary electrode mounted within said probe in electrical contact with said reservoir and in spaced relation with both of the other aforesaid electrodes, polarizing means for connection between said auxiliary electrode and said working electrode to generate a polarizing potential which creates a double layer at said working electrode and causes a redox reaction involving molecules of said gas which are present therein, switching means for periodically making and thereafter breaking said connection of said polarizing means, so that a series of current pulses flow at said working electrode, each said pulse comprising a forward flow of polarizing current, a flow of reaction current and a reverse flow of polarizing current, feedback means connected to said reference electrode for adjusting said polarizing potential to compensate for current flow effects at said auxiliary electrode, and charge measuring means for measuring the net charge transferred by said working electrode during the full period of one of said pulses.

7. Apparatus according to claim 6 wherein said charge measuring means comprises a capacitor connected for receiving a flow of current corresponding to the current in said pulses, means for measuring the voltage across said capacitor, and means for periodically discharging said capacitor.

8. Apparatus according to claim 7 and further comprising a differential amplifier having an output terminal connected to one side of said capacitor, one input terminal interconnecting a second side of said capacitor with said working electrode, and a second input terminal connected to a source of predetermined potential.

9. Apparatus according to claim 8 wherein said second input terminal is connected to a source of ground potential, so that said operational amplifier maintains said active electrode at a virtual ground potential.

10. Apparatus according to claim 6 wherein said reference electrode is screened from said auxiliary electrode.

11. Apparatus according to claim 6 wherein said working electrode screens said reference electrode from said auxiliary electrode.

12. Apparatus according to claim 11 wherein said charge measuring means comprises a capacitor connected for receiving a flow of current corresponding to the current in said pulses, means for measuring the voltage across said capacitor, and means for periodically discharging said capacitor.

13. Apparatus for measuring the concentration of oxygen in a liquid comprising:

a probe body of generally cylindrical configuration, constructed of electrically insulative material and having a rounded face provided with a reservoir defined by a generally circular channel an oxygen permeable membrane secured to said probe body and covering said face, an electrolyte filling said reservoir and wetting said face and the inner surface of said membrane, said electrolyte being a solvent for oxygen and being buffered to maintain a fixed concentration of hydrogen ions, a cathode mounted in said probe body centrally of said face and in electrical contact with said electrolyte, a reference electrode mounted within said probe body in electrical contact with said electrolyte and in spaced relation with said cathode, an auxiliary electrode mounted within said probe body in electrical contact with electrolyte and in spaced relation with said cathode opposite said reference electrode, polarizing means for generating a voltage of sufficient magnitude to polarize said cathode and supply a reaction current to cause reduction of oxygen molecules which come into contact with said cathode, switching means for alternately connecting said cathode and said auxiliary electrodes across said polarizing means and then to a source of common potential, so that said cathode becomes cyclically polarized, supplies said reaction current for a predetermined period of time and then becomes fully discharged, and charge measuring means for measuring the net charge flowing through said cathode during a substantially full cycle of said switching means.

14. Apparatus according to claim 13 wherein said electrodes are buried in said probe body and have distal ends which reach conformingly to said face.

15. Apparatus according to claim 14 wherein said cathode screens said reference electrode from said auxiliary electrode.

16. Apparatus according to claim 15 wherein said switching means comprises means for polarizing said cathode for a duration of approximately 40 milliseconds at a cyclical rate of approximately once every 4 records.

17. Apparatus according to claim 16 wherein said charge measuring means comprises a capacitor and means for measuring the voltage across said capacitor.

18. Apparatus according to claim 17 wherein said face is rounded to follow a spherical contour having a radius of approximately 1 inch.

19. Apparatus according to claim 18 wherein said switching means comprises means for holding said cathode at a virtual ground potential and means for applying a potential to said auxiliary electrode which alternates between ground and a positive value of approximately 1 volt.

* * * * *